US012565470B2

(12) United States Patent
Preuss et al.

(10) Patent No.: US 12,565,470 B2
(45) Date of Patent: Mar. 3, 2026

(54) METHOD OF PRODUCING A LOW GLYCIDOL MONOGLYCERIDE COMPOSITION AND THE LOW GLYCIDOL MONOGLYCERIDE COMPOSITION AS SUCH

(71) Applicant: PALSGAARD A/S, Juelsminde (DK)

(72) Inventors: Lars Preuss, Juelsminde (DK); Andrea Höhnke, Juelsminde (DK); Claus Hviid Christensen, Juelsminde (DK)

(73) Assignee: Palsgaard A/S (DK)

( * ) Notice: Subject to any disclaimer, the term of this patent is extended or adjusted under 35 U.S.C. 154(b) by 988 days.

(21) Appl. No.: 17/619,374

(22) PCT Filed: Jun. 18, 2020

(86) PCT No.: PCT/EP2020/066989
§ 371 (c)(1),
(2) Date: Dec. 15, 2021

(87) PCT Pub. No.: WO2020/254506
PCT Pub. Date: Dec. 24, 2020

(65) Prior Publication Data
US 2022/0227695 A1 Jul. 21, 2022

(30) Foreign Application Priority Data

Jun. 18, 2019 (EP) ...................................... 19180792

(51) Int. Cl.
*C07C 68/08* (2006.01)
*C07C 69/02* (2006.01)

(52) U.S. Cl.
CPC .............. *C07C 68/08* (2013.01); *C07C 69/02* (2013.01)

(58) Field of Classification Search
CPC ........... C07C 68/08; C07C 69/02; C11B 3/04; C11B 3/12; C11B 3/001; C11C 1/10; C11C 1/103; C11C 3/06
See application file for complete search history.

(56) References Cited

U.S. PATENT DOCUMENTS

| | | | |
|---|---|---|---|
| 6,235,742 B1 | 5/2001 | Bell et al. | |
| 2007/0129560 A1* | 6/2007 | Sawada ..................... | C11C 3/10 |
| | | | 554/174 |
| 2013/0323394 A1 | 12/2013 | Bruse et al. | |

FOREIGN PATENT DOCUMENTS

| | | | | |
|---|---|---|---|---|
| CA | 3068749 A1 | 1/2019 | | |
| CN | 1585814 A | 2/2005 | | |
| CN | 102010786 A | 4/2011 | | |
| CN | 102711496 A | 10/2012 | | |
| CN | 104159454 A | 11/2014 | | |
| CN | 104507325 A | 4/2015 | | |
| EP | 3424346 A1 | 1/2019 | | |
| JP | 2005504862 A | 2/2005 | | |
| JP | 2013512998 A | 4/2013 | | |
| WO | WO-03029392 A1 * | 4/2003 | ........... | C11B 7/0008 |
| WO | 2011069028 A1 | 6/2011 | | |
| WO | 2020150661 A1 | 7/2020 | | |

* cited by examiner

*Primary Examiner* — Deborah D Carr

(74) *Attorney, Agent, or Firm* — Elmore Patent Law Group, P.C.; Joseph C. Zucchero; Carolyn S. Elmore

(57) ABSTRACT

The present invention pertains to a method of producing monoglyceride compositions having a low glycidol content. The invention furthermore pertains to such monoglyceride compositions which can be obtained by the method.

27 Claims, 6 Drawing Sheets

METHOD OF PRODUCING A LOW GLYCIDOL MONOGLYCERIDE COMPOSITION AND THE LOW GLYCIDOL MONOGLYCERIDE COMPOSITION AS SUCH

FIELD OF THE INVENTION

The present invention pertains to a method of producing monoglyceride compositions having a low glycidol content. The invention furthermore pertains to monoglyceride compositions which can be obtained by the method.

BACKGROUND

Industrial production of monoglycerides is accompanied by formation of glycidol and glycidyl esters. These by-products have recently been found to be less desired. However, until now attempts to remove glycidol and glycidyl esters from monoglyceride products have been unsuccessful. Glycidol and glycidyl esters are generated due to processes occurring at the elevated temperatures that are typically used for producing monoglyceride products.

SUMMARY OF THE INVENTION

The present inventors have discovered that the level of glycidol and glycidyl esters of monoglyceride products can be reduced by using a thermal treatment but using lower temperatures than required for production of the monoglycerides. This is highly surprising as the higher temperature conditions during the production appears to be the cause of the glycidol problem.

The inventors have furthermore found that the level of glycidol and glycidyl esters can be reduced by contacting a monoglyceride product with a solid acidic material, and that this contact advantageously can be used in combination with the thermal treatment.

Thus, an aspect of the invention pertains to method of producing a monoglyceride-containing product comprising at least 25% w/w monoglyceride and having a low content of glycidol equivalents, the method comprising step i) of thermally treating a first monoglyceride-containing composition (mcc1) comprising at least 25% w/w monoglyceride and a total content of glycidol equivalents of at least 1 ppm, said thermal treatment involves heating the monoglyceride-containing composition to a temperature in the range of 90-210 degrees C. for a duration sufficient to reduce the total content of glycidol equivalents by at least 50%, and/or step ii) of contacting a second monoglyceride-containing composition (mcc2) comprising at least 25% w/w monoglyceride and a total content of glycidol equivalents of at least 1 ppm with a solid acidic material which preferably is insoluble in monoglyceride.

Another aspect of the invention pertains to a monoglyceride-containing product obtainable by the method described herein.

Yet an aspect of the invention pertains to the use of step i) and/or step ii) for producing a monoglyceride-containing product comprising at least 25% w/w monoglyceride and having a low content of glycidol equivalents; wherein step i) involves thermally treating a first monoglyceride-containing composition comprising at least 25% w/w monoglyceride, said thermal treatment involves heating the monoglyceride-containing composition to a temperature in the range of 90-210 degrees C. for a duration sufficient to reduce the total content of glycidol equivalents by at least 50%, and wherein step ii) involves contacting a second monoglyceride-containing composition comprising at least 25% w/w monoglyceride with a solid acidic material which preferably is insoluble in monoglyceride.

DETAILED DESCRIPTION

Figure 1:
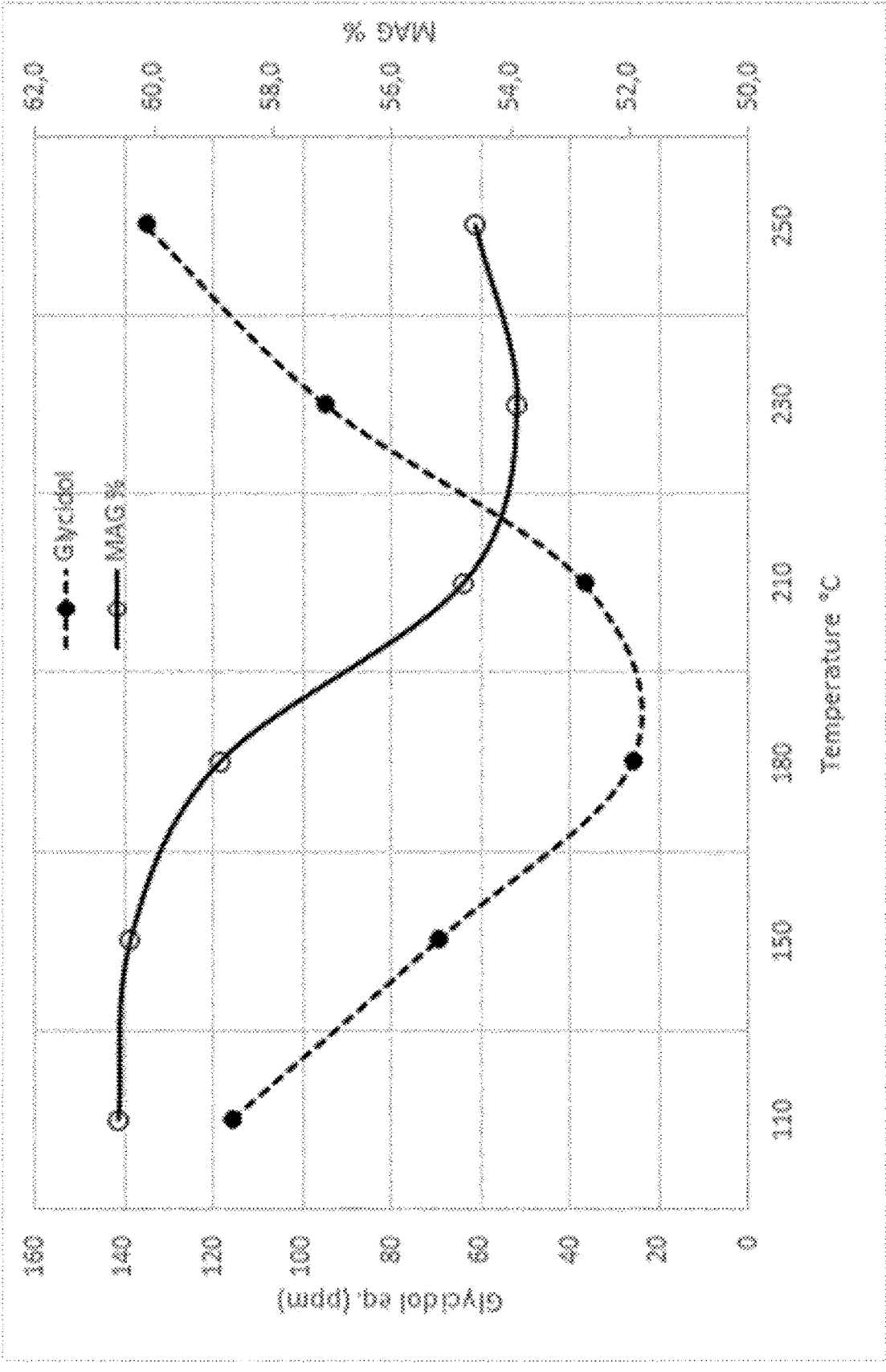
FIG. 1 shows how thermal treatment at different temperatures affects the glycidol content and the content of monoglyceride (MAG).

An aspect of the invention pertains to a method of producing a monoglyceride-containing product comprising at least 25% w/w monoglyceride and having a low content of glycidol equivalents, the method comprising:

step i) of thermally treating a first monoglyceride-containing composition (mcc1) comprising at least 25% w/w monoglyceride and a total content of glycidol equivalents of at least 2 ppm, said thermal treatment involves heating the monoglyceride-containing composition to a temperature in the range of 90-210 degrees C. for a duration sufficient to reduce the total content of glycidol equivalents by at least 50%, and/or step ii) of contacting a second monoglyceride-containing composition (mcc2) comprising at least 25% w/w monoglyceride and a total content of glycidol equivalents of at least 1 ppm with a solid acidic material which is preferably is insoluble in monoglyceride.

In the context of the present invention the term "monoglyceride-containing product" pertains to a composition that primarily contains partial glycerides including at least 25% w/w monoglyceride.

In the context of the present invention the term "glycidol" pertains to the compound with the IUPAC name 2,3-epoxy-propan-1-ol and contains both an epoxide group and an alcohol group.

In the context of the present invention the term "glycidol equivalents" pertains to both free glycidol and glycidyl esters. The total content of glycidol equivalents is measured according to Analysis 1.1.

In the context of the present invention the term "monoglyceride-containing product having a low content of glycidol equivalents" has a content of glycidol equivalents of at most 10 ppm.

In the context of the present invention the term "mono-glyceride-containing composition" pertains to a composition that contains at least 25% w/w monoglyceride and prefer-ably at least 50% w/w glycerides. A monoglyceride-con-taining composition typically also contains diglyceride and triglyceride and optionally glycerol.

In the context of the present invention, the phrase "Y and/or X" means "Y" or "X" or "Y and X". Along the same line of logic, the phrase "$n_1$, $n_2$, $n_{i-1}$, and/or $n_i$" means "$n_1$" or "$n_2$" or . . . or "$n_{i-1}$" or "$n_i$" or any combination of the components $n_1$, $n_2$, . . . $n_{i-1}$, and $n_i$.

In some preferred embodiments of the invention the method comprises step i) and optionally also step ii). How-ever it may also be preferred that the method contains step i) but not step ii).

In other preferred embodiments of the invention the method comprises step ii) and optionally also step i). How-ever it may also be preferred that the method contains step ii) but not step i).

In some particularly preferred embodiments of the inven-tion method comprises both step i) and step ii), preferably implemented as step i) following by step ii).

Alternatively, but also preferred, steps i) and ii) may be performed simultaneously on the same mcc, in which case the mcc1 and mcc2 is the same composition.

As mentioned above, step i) involves thermally treating a first monoglyceride-containing composition (mcc1) com-prising at least 25% w/w monoglyceride and a total content of glycidol equivalents of at least 2 ppm, said thermal treatment involves heating the monoglyceride-containing composition to a temperature in the range of 90-210 degrees C. for a duration sufficient to reduce the total content of glycidol equivalents at least 50%.

The thermal treatment of step i) preferably involves heating the first monoglyceride-containing composition to a temperature in the range of 95-195 degrees C., more pref-erably 100-180 degrees C., even more preferably 120-170 degrees C., and most preferably 140-160 degrees C.

The thermal treatment of step i) preferably involves heating the first monoglyceride-containing composition for a duration sufficient to reduce the total content of glycidol equivalents of mcc1 by at least 60%, more preferably by at least 70%, even more preferably by at least 80%, and most preferably by at least 90%. Even higher levels reduction may be required and the thermal treatment of step i) therefore preferably involves heating the first monoglyceride-contain-ing composition for a duration sufficient to reduce the total content of glycidol equivalents of mcc1 by at least 95%, and more preferably by at least 99%, and even more preferably by at least 99.9%.

The thermal treatment of step i) is preferably performed using an inert atmosphere. An inert atmosphere preferably has a partial pressure of oxygen which is lower than that of atmospheric air (which typically is approx. 0.2 bar). An inert atmosphere may e.g. be obtained by creating a vacuum and/or by using a suitable inert gas such as e.g. nitrogen, argon or carbon dioxide.

The inert atmosphere may contain a partial pressure of oxygen of at most 0.1 bar, preferably at most 0.05 bar, more preferred at most 0.01 bar, even more preferred at most 0.001 bar and most preferred at most 0.0001 bar.

The use of inert atmosphere is e.g. useful to avoid formation of peroxides and other degradation products dur-ing processing.

Alternatively or additionally suitable antioxidants may be added during processing and may form part of the mcc1 to avoid or reduce oxidation.

As mentioned above step ii) involves contacting a second monoglyceride-containing composition (mcc2) comprising at least 25% w/w monoglyceride and a total content of glycidol equivalents of at least 1 ppm with a solid acidic material, which preferably is insoluble in monoglyceride.

The temperature and contact time of step ii) is preferably chosen so the content of glycidol equivalents of the mcc2 is reduced by at least 50%, preferably by at least 70%, even more preferred by at least 80% and most preferably by at least 90%. Even higher levels reduction may be required and step ii) therefore preferably involves contacting the second monoglyceride-containing composition with the solid acidic material for a duration sufficient to reduce the total content of glycidol equivalents of mcc by at least 95%, more preferably by at least 99%, and even more preferably by at least 99.9%.

If the content of glycidol equivalents is reduced by e.g. 75% it means that the content of glycidol equivalents after step ii) is 75% lower than the content of glycidol equivalents of the mcc2.

Step ii) is also preferably performed using an inert atmo-sphere, particularly if combined with thermal treatment.

In the context of the present invention the term "solid acidic material" is a material that is solid at at least 50 degrees C., preferably at at least 100 degrees C. and more preferably at at least 210 degrees C., and that furthermore are capable of acting as an acid. The solid acidic material may e.g. be a purified acid on solid form. Alternatively, but preferably the solid acidic material may contain a matrix material and furthermore have a surface containing acidic functional groups. The matrix material need not be acidic as such but is preferably insoluble in monoglyceride.

Solid acidic materials are well-known to the skilled person and are e.g. described in chapters 2 and 3 of "*Solid Acid Catalysis: From Fundamentals to Applications*", H. Hattori, Y. Ono, 2015 (Hattori 2015), which is incorporated herein by reference for all purposes. It is particularly pre-ferred that the solid acidic material is defined as in pages 23-36 of Hattori 2015.

In some preferred embodiments of the invention the solid acidic material is insoluble in monoglyceride.

In the context of the present invention the term "insoluble in monoglyceride" means that the solid acidic material in question has a solubility of most 1 g/kg in glycerol mono oleate at a temperature of 100 degree C. and at atmospheric pressure.

Preferably the solid acidic material has a solubility of most 0.1 g/kg in glycerol mono oleate at a temperature of 100 degree C. and at atmospheric pressure, more preferably at most 0.01 g/kg, and even more preferably at most 0.001 g/kg In some preferred embodiments of the invention the solid acidic material of step ii) has is used in an amount of 0.1-10% w/w relative to the weight of the mcc2, more preferably 0.5-8% w/w, even more preferably 1-6% w/w and more preferably 2-5% w/w relative to the weight of the mcc2.

The solid acidic material is preferably characterized as described in Chapter 3 in "Solid Acid Catalysis: From Fundamentals to Applications", H. Hattori, Y. Ono, 2015.

In some preferred embodiments of the invention step ii) involves heating the second monoglyceride-containing com-position to a temperature in the range of 50-180 degrees C., more preferably 60-160 degrees C., even more preferably 70-140 degrees C., and most preferably 80-120 degrees C.

Temperatures above 180 degrees C. give rise to increasing degrees of monoglyceride revertation which e.g. may convert two monoglyceride molecules to a diglyceride molecule and a glycerol molecule. Such revertation is preferably avoided or at least reduced, particularly during step ii).

The contact time between the solid acidic material and the mcc2 is selected to obtain the desired degree of reduction of glycidol equivalents. The contact time is preferably at most 24 hours, more preferred at most 12 hours, even more preferred at most 6 hours and most preferred at most 4 hours. The contact time is preferably in the range of 1 minute to 24 hours, more preferably in the range of 2 minutes to 12 hours, even more preferred in the range of 5 minutes-6 hours, and most preferably 10 minutes to 4 hours.

The contact between the solid acidic material and the mcc2 may be implemented in a number of different ways. The solid acidic material may e.g. be arranged in a packed column or form part of a stationary phase through which the mcc2 is flowed. Alternatively, the solid acidic material may be in the form of small particles dispersed into the mcc2 and contact the mcc2 which the mixture is agitated, e.g. by stirring. The solid acidic material is preferably recovered once step ii) has been completed. The solid acidic material is preferably reused and may require regeneration after some time of operation.

It is particularly preferred that the solid acidic material is a heterogeneous acid catalyst, that catalyses the conversion of glycidol and/or glycidyl esters.

The solid acidic material of step ii) is preferably selected from one or more of the group consisting of zeolites, zeotypes, acid clays, metal oxides, mixed metal oxides, sulphated oxides, supported acids, cation exchange resins, and a combination thereof.

For example, the solid acidic material of step ii) comprises, or even consist of acidic X- or Y-zeolites, mordenite, Zeolite Socony Mobil-5 (ZSM-5) or a combination thereof.

It is particularly preferred that the solid acidic material of step ii) comprises, or even consists of Aluminophospates (AlPO), silicoaluminimophosphate (SAPO), or a combination thereof.

In some preferred embodiments of the invention the solid acidic material of step ii) comprises acid bleaching clay, acid pillared clays, or a combination thereof.

In some preferred embodiments of the invention the solid acidic material of step ii) comprises $Al_2O_3$, $ZrO_2$, or a combination thereof.

In some preferred embodiments of the invention the solid acidic material of step ii) comprises or even consists of crystalline $SiO_2$—$Al_2O_3$, crystalline $SiO_2$—$ZrO_2$, amorphous $SiO_2$—$Al_2O_3$, or a combination thereof.

In some preferred embodiments of the invention the solid acidic material of step ii) comprises sulphated $ZrO_2$.

In other preferred embodiments of the invention the solid acidic material of step ii) comprises triflic acid, sulphuric acid or sulphonic acid supported on $SiO_2$ or $ZrO_2$.

In some preferred embodiments of the invention the solid acidic material of step ii) comprises, or even consists of, a sulfonated matrix, such as e.g. a sulfonated tetrafluoroethylene based fluoropolymer-copolymer (e.g. NAFION").

The first and/or second monoglyceride-containing composition preferably comprises:
    at least 25% w/w monoglyceride,
    at least 1 ppm glycidol equivalents, and
    glycerol, diglyceride, and triglyceride.

In some preferred embodiments of the invention the first and/or second mcc comprises at least 30% w/w monoglyceride, more preferably at least 34% w/w, even more preferably at least 40%, and most preferably at least 50% w/w.

Even higher concentrations of monoglyceride may be preferred and in some preferred embodiments of the invention the first and/or second mcc comprises at least 80% w/w monoglyceride, more preferably at least 90% w/w, even more preferably at least 95%, and most preferably at least 97% w/w.

In some preferred embodiments of the invention the first and/or second mcc comprises at most 30% w/w glycerol, more preferably at most 25% w/w, even more preferably at most 15%, and most preferably at most 5% w/w.

Even less glycerol may be preferred, particularly in the content of step ii), thus in some preferred embodiments of the invention the first and/or second mcc comprises at most 5% w/w glycerol, more preferably at most 2% w/w, even more preferably at most 0.5%, and most preferably at most 0.1% w/w.

In some preferred embodiments of the invention the first and/or second mcc comprises at most 30% w/w triglyceride, more preferably at most 20% w/w triglyceride, even more preferably at most 10% w/w triglyceride, and most preferably at most 5% w/w triglyceride.

Even less triglyceride may be required, thus in some preferred embodiments of the invention the first and/or second mcc comprises at most 4% w/w triglyceride, more preferably at most 2% w/w triglyceride, even more preferably at most 0.5% w/w triglyceride, and most preferably at most 0.1% w/w triglyceride.

In some preferred embodiments of the invention the first and/or second mcc comprises total amount of monoglyceride and diglyceride of at least 50% w/w, more preferably at least 60% w/w, even more preferably at least 70%, and most preferably at least 80% w/w.

In some preferred embodiments of the invention the first and/or second mcc has a content of glycidol equivalents of at least 1 ppm. The first and/or second mcc furthermore has a content of glycidol equivalents higher than that of the monoglyceride-containing product, preferably at least 20% higher, more preferably at least 50% higher, even more preferably at least 100% higher, and most preferably at least 200% higher.

In some preferred embodiments of the invention the first and/or second mcc comprises an amount of glycidol equivalents at least 2 ppm, more preferably at least 5 ppm, even more preferably at least 10 ppm and most preferably at least 15 ppm. Even higher contents of glycidol equivalents can be reached and in some preferred embodiments of the invention the first and/or second mcc comprises an amount of glycidol equivalents at least 25 ppm, more preferably at least 50 ppm, even more preferably at least 100 ppm and most preferably at least 200 ppm.

In some preferred embodiments of the invention the first and/or second mcc comprises an amount of glycidol equivalents of 1-2000 ppm, more preferably 5-1000 ppm, even more preferably 10-800 ppm and most preferably 20-600 ppm. For example, the first and/or second mcc may preferably comprises an amount of glycidol equivalents of 50-500 ppm, and more preferably 100-300 ppm.

In some preferred embodiments of the invention the first and/or second mcc has an iodine value of at least 20 more preferably at least 40, even preferably at least 60, and most preferably at least 75. It may for example preferred that the mcc1 has an iodine number of 20-200 more preferably 40-150, even more preferably 60-140 and most preferably 75-120.

In other preferred embodiments of the invention the first mcc has an iodine value of at less than 20, more preferably at most 15, even preferably at most 10, and most preferably at most 5.

In some preferred embodiments of the invention the first and/or second mcc has a peroxide value of at most 10 meq/kg, more preferably at most 5 meq/kg, even preferably at most 2 meq/kg, and most preferably at most 1 meq/kg. It is furthermore preferred that the raw materials used for preparing the mcc equally have a low peroxide value preferably at most 10 meq/kg, more preferably at most 5 meq/kg, even preferably at most 2 meq/kg, and most preferably at most 1 meq/kg.

It is particularly preferred that the method of the invention comprises the following steps:

a) contacting glycerol with diglyceride and/or triglyceride at conditions sufficient to provide a reacted mixture comprising:
at least 25% w/w monoglyceride,
at least 1% w/w glycerol,
diglyceride and/or triglyceride, and
a content of glycidol equivalents of at least 1 ppm, b) subjecting a composition derived from the reacted mixture of step a) to a distillation to remove an amount of glycerol, thereby providing a first distillate enriched with respect to glycerol, and a first distillation residue enriched with respect to monoglyceride, c) optionally, subjecting the first distillation residue to a distillation to further enrich monoglyceride thereby providing a second distillate enriched with respect to monoglyceride and a second distillation residue depleted with respect to diglyceride, d) optionally, further purifying the first distillation residue and/or the second distillate, and recovering the first distillation residue of step b), the second distillate of step c), or a further purified composition of step d) as the monoglyceride-containing product, and wherein the first and/or second monoglyceride-containing composition is a composition derived from step a), b), c), or d).

In the context of the present invention the term a "composition derived from" a previous composition contains at least a significant portion of the monoglyceride of the previous composition and preferably has substantially the same or an even higher weight ratio between monoglyceride and diglyceride than the previous composition.

A "composition derive from" a previous composition preferably contains at least 50% w/w of the monoglyceride of the previous composition, more preferably at least 70% w/w, even more preferably at least 90% w/w, and most preferably at least 95% w/w of the monoglyceride of the previous composition.

In preferred embodiments of the invention a "composition derive from" a previous composition is the previous composition as such or a monoglyceride concentrate thereof.

In the context of the present invention the term "monoglyceride concentrate" of a previous composition pertains a composition prepared by processing the previous composition to contain a higher absolute concentration of monoglyceride than the previous composition. Such method for concentrating monoglyceride is well-known to the skilled person and includes e.g. phase separation.

In some preferred embodiments of the invention the composition derived from the reacted mixture of step a) is derived by removing at least some of the glycerol from the reacted mixture of step a), preferably by separation of a liquid glycerol phase.

As mentioned above step a) involves contacting glycerol with diglyceride and/or triglyceride at conditions sufficient to provide a reacted mixture comprising:
at least 25% w/w monoglyceride,
at least 1% w/w glycerol,
diglyceride and/or triglyceride, and
a content of glycidol equivalents of at least 1 ppm.

The process for producing monoglycerides is well-known to the skilled person and the contact of step a) is typically performed at a temperature in the range of 220-300 degrees C., and more preferably in the range of 250-300 degrees C. Contact is often performed in the presence of a suitable catalyst and at a pressure that facilitates the formation of monoglycerides.

In some preferred embodiments of the invention the reacted mixture of step a) furthermore comprises one or more of:
a reacted mixture containing:
10-50% w/w diglyceride,
1-30% w/w triglyceride, and
0-10% w/w free fatty acids.

In some preferred embodiments of the invention the reacted mixture of step a) comprises:
25-60% w/w monoglyceride,
10-50% w/w diglyceride,
1-30% w/w triglyceride,
1-25% w/w glycerol,
0-10% w/w free fatty acids, and
a content of glycidol equivalents of at least 1 ppm.

The reacted mixture of step a) preferably comprises an amount of glycidol equivalents at least 5 ppm, more preferably at least 10 ppm, even more preferably at least 15 ppm and most preferably at least 20 ppm.

Even higher contents of glycidol equivalents can be reached and in some preferred embodiments of the invention the reacted mixture of step a) comprises an amount of glycidol equivalents at least 50 ppm, more preferably at least 100 ppm, even more preferably at least 150 ppm and most preferably at least 200 ppm.

In some preferred embodiments of the invention the reacted mixture of step a) comprises an amount of glycidol equivalents of 1-2000 ppm, more preferably 5-1000 ppm, even more preferably 10-800 ppm and most preferably 20-600 ppm. For example, the reacted mixture of step a) may preferably comprises an amount of glycidol equivalents of 50-500 ppm, and more preferably 100-300 ppm.

In some preferred embodiments of the invention the reacted mixture of step a) has a total amount of monoglyceride and diglyceride of at least 50% w/w, more preferably at least 60% w/w, even more preferably at least 70% w/w, and most preferably at least 80% w/w.

In some preferred embodiments of the invention the reacted mixture of step a) has an iodine value of at least 20 more preferably at least 40, even preferably at least 60, and most preferably at least 75. It may for example be preferred that the reacted mixture of step a) has an iodine number of 20-200 more preferably 40-150, even more preferably 60-140 and most preferably 75-120.

In other preferred embodiments of the invention the reacted mixture of step a) has an iodine value of at less than 20, more preferably at most 15, even preferably at most 10, and most preferably at most 5.

In some preferred embodiments of the invention the reacted mixture of step a) has a peroxide value of at most 10 meq/kg, more preferably at most 5 meq/kg, even preferably at most 2 meq/kg, and most preferably at most 1 meq/kg. It is furthermore preferred that the raw materials used for preparing the reacted mixture of step a) equally have a low peroxide value preferably at most 10 meq/kg, more preferably at most 5 meq/kg, even preferably at most 2 meq/kg, and most preferably at most 1 meq/kg.

As described above step b) involves subjecting a composition derived from the reacted mixture of step a) to a distillation to remove an amount of glycerol, thereby providing a first distillate enriched with respect to glycerol, and a first distillation residue enriched with respect to monoglyceride.

In some preferred embodiments of the invention the composition derived from the reacted mixture of step a) which is distilled in step b) comprises:

25-80% w/w monoglyceride,
10-50% w/w diglyceride,
1-30% w/w triglyceride,
1-25% w/w glycerol,
0-10% w/w free fatty acids, and
a content of glycidol equivalents of at least 1 ppm.

The distillation of step b) may e.g. involve continuous trayed, thin-layer, packed column or short path distillation. Suitable temperatures and pressures are preferably in the range of 100-210 degrees C. at 0.001-50 mbar, more preferred in the range of 110-190 degrees C. and 0.01-20 mbar, and even more preferred in the range of 120-170 degrees C. and 0.1-10 mbar. Overheated steam may e.g. be used to increase removal of glycerol on a trayed or packed distillation column.

As mentioned above, the method of the invention may optionally contain a step c) of subjecting the first distillation residue to a distillation to further enrich monoglyceride thereby providing a second distillate enriched with respect to monoglyceride and a second distillation residue depleted with respect to diglyceride.

Thus in some preferred embodiments of the invention the method of the invention contains a step c) of subjecting the first distillation residue to a distillation to further enrich monoglyceride thereby providing a second distillate enriched with respect to monoglyceride and a second distillation residue depleted with respect to diglyceride.

However, in other preferred embodiments of the invention the method does not contain step c).

The distillation of step c) may e.g. be implemented as a continuous short path distillation using temperatures and pressures in the range of at 150-250 degrees C. and 0.0001-10 mbar, preferably 160-230 degrees C. and 0.001-1 mbar, and even more preferably 170-220 degrees C. and 0.001-0.1 mbar.

As mentioned above, the method of the invention optionally contains d) further purification of the first distillation residue and/or the second distillate.

Thus in some preferred embodiments of the invention the method of the invention contains a step d). However, in other preferred embodiments of the invention the method does not contain step d).

The further purification may e.g. involve steam stripping on a packed or trayed distillation column, bleaching using adsorptive bleaching agents such as bleaching earth and/or reducing bleaching agents such as hydrogen peroxide, sodium borohydride or sodium hypophosphite In some preferred embodiments of the invention the method comprises at least step i) and step i) is performed during or prior to step b).

In some preferred embodiments of the invention the method comprises at least step i) and step c) and step i) is performed prior to the distillation of step c).

In some preferred embodiments of the invention the method comprises at least step i) and step d) and step i) is performed prior to the further purification of step d).

In some preferred embodiments of the invention the method of the invention comprises at least step ii) and step ii) is performed after step b) and preferably after step c) and/or d) if they form part of the method.

The present inventors have found that it is advantageous to perform step ii) on compositions having a relatively low concentration of glycerol. Thus it is preferred that the mcc2 has a content of glycerol of at most 10% w/w, more preferably at most 5% w/w, even more preferably at most 1% w/w, and most preferably at most 0.5% w/w.

If not used directly after production the monoglyceride-containing product is preferably packaged in a suitable container. This may for example be the container of a bulk delivery in truck, an intermediate bulk container, a drum, a can, a bag, or a box. If a box is used it preferably has a polymer liner inside contacting the monoglyceride-containing product. If the monoglyceride-containing product is transferred to the container of a bulk delivery in truck it is often preferred that monoglyceride-containing product is kept at a temperature sufficient to keep it in liquid state during storage and transport.

Another aspect of the invention pertains to a monoglyceride-containing product, e.g. obtainable according to the method described herein.

The monoglyceride-containing product preferably comprises:

at least 80% w/w monoglyceride,
at most 1 ppm glycidol equivalents, and
optionally, glycerol, diglyceride, and triglyceride.

In some preferred embodiments of the invention the monoglyceride-containing product comprises at least 50% w/w monoglyceride, more preferably at least 60% w/w, even more preferably at least 70%, and most preferably at least 75% w/w.

Even higher concentrations of monoglyceride may be preferred and in some preferred embodiments of the invention the monoglyceride-containing product comprises at least 80% w/w monoglyceride, more preferably at least 90% w/w, even more preferably at least 95%, and most preferably at least 97% w/w.

In some preferred embodiments of the invention the monoglyceride-containing product comprises at most 5% w/w glycerol, more preferably at most 2% w/w, even more preferably at most 0.5%, and most preferably at most 0.1% w/w.

In some preferred embodiments of the invention the monoglyceride-containing product comprises a total amount of water of at most 2% w/w, more preferably at most 1% w/w, even more preferably at most 0.3%, and most preferably at most 0.1% w/w.

In some preferred embodiments of the invention the monoglyceride-containing product comprises at most 5% w/w triglyceride, more preferably at most 2% w/w triglyceride, even more preferably at most 0.5% w/w triglyceride, and most preferably at most 0.1% w/w triglyceride.

In some preferred embodiments of the invention the monoglyceride-containing product comprises a total amount of monoglyceride and diglyceride of at least 70% w/w, more preferably at least 60% w/w, even more preferably at least 70%, and most preferably at least 80% w/w.

Even higher concentrations of monoglyceride may be preferred and in some preferred embodiments of the invention the monoglyceride-containing product a total amount of monoglyceride and diglyceride of at least 80% w/w monoglyceride, more preferably at least 90% w/w, even more preferably at least 95%, and most preferably at least 97% w/w.

In some preferred embodiments of the invention the monoglyceride-containing product has a content of glycidol equivalents of at most 10 ppm, more preferably at most 5 ppm, even more preferably at most 1 ppm, and most preferably at most 0.5 ppm.

The inventors have demonstrated that the present invention makes it possible to achieve even lower content of glycidol equivalents and in some preferred embodiments of the invention the monoglyceride-containing product has a content of glycidol equivalents of at most 0.3 ppm, more preferably at most 0.1 ppm, even more preferably at most 0.05 ppm, and most preferably at most 0.02 ppm.

In some preferred embodiments of the invention the monoglyceride-containing product has an iodine value of at least 20 more preferably at least 40, even preferably at least 60, and most preferably at least 75. It may for example preferred that the monoglyceride-containing product has an iodine number of 20-200 more preferably 40-150, even more preferably 60-140 and most preferably 75-120.

In other preferred embodiments of the invention the monoglyceride-containing product has an iodine value of at less than 20, more preferably at most 15, even preferably at most 10, and most preferably at most 5.

In some preferred embodiments of the invention the monoglyceride-containing product has a peroxide value of at most 10 meq/kg, more preferably at most 5 meq/kg, even preferably at most 2 meq/kg, and most preferably at most 1 meq/kg.

The inventors have found that the present invention is particularly useful for producing monoglyceride-containing product having a high content of monoglyceride, a low content of glycidol equivalents.

Thus in some particularly preferred embodiments of the invention the monoglyceride-containing product comprises:
    at least 90% w/w monoglyceride, more preferably 95% w/w monoglyceride, and even more preferably at least 97% w/w monoglyceride, and
    a content of glycidol equivalents of at most 10 ppm, more preferably at most 5 ppm, even more preferably at most 1 ppm, and most preferably at most 0.5 ppm.

The inventors have furthermore found that the present invention is particularly useful for producing monoglyceride-containing product having a high content of monoglyceride, a low content of glycidol equivalents, and a low peroxide value. This is even more pronounced when producing monoglyceride-containing products having a high degree of unsaturation which is more prone to peroxide formation.

Thus in some particularly preferred embodiments of the invention the monoglyceride-containing product comprises:
    at least 90% w/w monoglyceride, more preferably 95% w/w monoglyceride, and even more preferably at least 97% w/w monoglyceride,
    a content of glycidol equivalents of at most 10 ppm, more preferably at most 5 ppm, even more preferably at most 1 ppm, and most preferably at most 0.5 ppm,
and having:
    a peroxide value of at most 10 meq/kg, more preferably at most 5 meq/kg, even preferably at most 2 meq/kg, and most preferably at most 1 meq/kg.

In other preferred embodiments of the invention the monoglyceride-containing product comprises:
    at least 90% w/w monoglyceride, more preferably 95% w/w monoglyceride, and even more preferably at least 97% w/w monoglyceride
    a content of glycidol equivalents of at most 10 ppm, more preferably at most 5 ppm, even more preferably at most 1 ppm, and most preferably at most 0.5 ppm, and having:
    a peroxide value of at most 10 meq/kg, more preferably at most 5 meq/kg, even preferably at most 2 meq/kg, and most preferably at most 1 meq/kg,
    an iodine value of at least 20, more preferably at least 40, even preferably at least 60, and most preferably at least 75.

Yet an aspect of the invention pertains the ese of step i) and/or step ii) for producing a monoglyceride-containing product comprising at least 25% w/w monoglyceride and having a low content of glycidol equivalents; wherein
    step i) involves thermally treating a first monoglyceride-containing composition comprising at least 25% w/w monoglyceride, said thermal treatment involves heating the monoglyceride-containing composition to a temperature in the range of 90-210 degrees C., preferably for a duration sufficient to reduce the total content of glycidol equivalents by at least 50%, and wherein
    step ii) involves contacting a second monoglyceride-containing composition comprising at least 25% w/w monoglyceride with a solid acidic material which preferably is insoluble in monoglyceride.

The above-mentioned use is preferably for reducing the content of glycidol equivalents in the mcc and consequently in the final monoglyceride-containing product.

The present invention has been described above with reference to specific embodiments and aspects. However, other embodiments than the above described are equally possible within the scope of the invention. The different features and steps of various embodiments and aspects of the invention may be combined in other ways than those described herein unless it is stated otherwise.

EXAMPLES

Analysis 1.1: Determination of the Content of Glycidol Equivalents
    The content of glycidol equivalents is determined according to AOCS Official Method Cd 29b-13 rev. 2017.
Analysis 1.2: Determination of the Amounts of Monoglyceride, Diglyceride, Triglyceride, Free Glycerol and Free Fatty Acids
    The amounts of monoglyceride (MAG), diglyceride (DAG), triglyceride (TAG), free glycerol and free fatty acids (FFA) are determined according to AOCS Official Method Cd 11b-91, Reapproved 2009.
Analysis 1.3: Determination of Peroxide Value
    The peroxide value of a sample is determined according to AOCS Official Method Cd 8b-90. The peroxide values are provided in the unit meq $H_2O_2$/kg sample
Analysis 1.4: Determination of Iodine Value
    The iodine value (IV) of a sample is determined according to AOAC Official Method 993.20 The iodine value is expressed as grams of iodine absorbed by the 100 g of the test portion following the specified procedure.
Analysis 1.5: Determination of Lovibond Color
    Lovibond color is measured according to AOCS Cc 13j-97. Samples are measured in a cuvette with a 25.4 mm (1 inch) cell path length.

Example 1: Traditional Process for Producing Monoglycerides and Diglycerides A traditional monoglyceride-containing product was produced using steps a), b), c) and d).

a) 90 g glycerol, 210 g. high oleic sunflower oil (Iodine value=80) and 0.75 g NaOH (s) was placed in a three-necked round bottomed flask with agitation. The reaction mixture was heated to 250 degrees C. at 500 mbar for 60 minutes after reaction temperature was reached. The hot reaction mixture was rapidly cooled to 80 degrees C. in an ice/water bath. 0.72 g H₃PO₄ (85% aqueous solution) was added under agitation, and the formed precipitate was removed by filtration. The reaction mixture was analyzed for composition and total glycidol content.

b) The reaction mixture from step a) was allowed to separate in a heating cabinet at 80 degrees C. for 60 min in a separating funnel. The lower glycerol phase was removed and discarded, and the upper glyceride phase was collected and analyzed for composition and total glycidol content.

c) The product from step b) was distilled on a UIC KDL 5 short path vacuum distillation plant at 130 degrees C. and 0.3 mbar pressure and the product was collected as residue. The product was analyzed for composition and total glycidol content.

d) The product from step c) was distilled on a UIC KDL 5 short path vacuum distillation plant at 170 degrees C. and 0.001 mbar pressure and the product was collected as distillate. The product was analyzed for composition and content of glycidol equivalents.

The results are summarized below:

| Example 1 | Free glycerol (FG) (w/w %) | Free fatty acids FFA (w/w %) | Monoglyceride MAG (w/w %) | Diglyceride DAG (w/w %) | Triglyceride TAG (w/w %) | Glycidol eq. (ppm) |
|---|---|---|---|---|---|---|
| a) | 19.1 | 0.2 | 53.4 | 24.3 | 3.0 | 75.2 |
| b) | 11.6 | 0.1 | 58.4 | 26.7 | 3.2 | 82.5 |
| c) | 0.5 | 0.2 | 64.7 | 30.7 | 3.9 | 44.2 |
| d) | 1.1 | 0.3 | 97.5 | 1.2 | 0.0 | 58.6 |

Example 2: Effect of Thermal Treatment at Different Temperatures

A product prepared as described in example 1b) was heated to 110, 150, 180, 210, 230 and 250 degrees C. for 10 min under N₂ then cooled rapidly to 25 degrees C. The product was analyzed for composition and content of glycidol equivalents. The results are summarized below and in FIG. 1:

| Example 2 | Free glycerol (FG) (w/w %) | Free fatty acids FFA (w/w %) | Monoglyceride MAG (w/w %) | Diglyceride DAG (w/w %) | Triglyceride TAG (w/w %) | Glycidol eq. (ppm) |
|---|---|---|---|---|---|---|
| No heating | 11.5 | 0.2 | 59.6 | 26.3 | 2.4 | 115.8 |
| 110 | 10.2 | 0.2 | 60.6 | 26.0 | 3.1 | 111.2 |
| 150 | 9.9 | 0.2 | 60.4 | 26.4 | 3.1 | 69.8 |
| 180 | 9.8 | 0.3 | 58.9 | 27.8 | 3.3 | 26.2 |
| 210 | 8.9 | 0.2 | 54.8 | 32.9 | 3.1 | 37.2 |
| 230 | 8.6 | 0.2 | 53.9 | 33.0 | 4.3 | 95.3 |
| 250 | 8.8 | 0.3 | 54.6 | 32.4 | 3.9 | 135.3 |

Conclusion

The most effective temperature for reduction of glycidol is approximately 180 degrees C. It is furthermore observed that the content of MAG is reduced when operating in the temperature range 180-250 degrees C.

Example 3: Thermal Treatment at 140 Degrees C. For Different Durations

Figure 2:
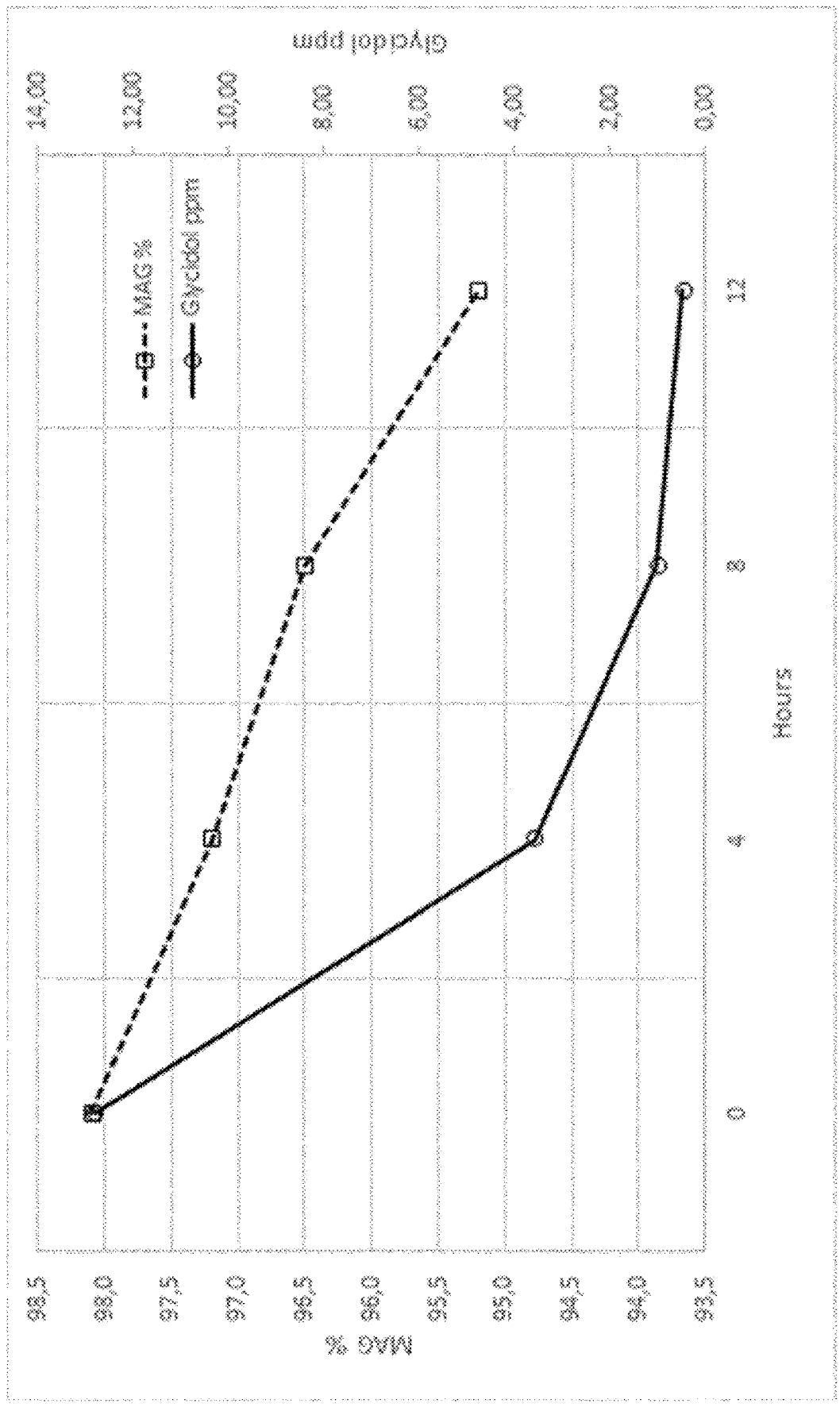
FIG. 2 shows how thermal treatment at 150 degrees C. for different durations affects the glycidol content and the content of MAG.

A product prepared as described in example 1d) was heated to 140 degrees C. under N₂ and samples were taken at 0, 4, 8 and 12 hours under N₂ then cooled rapidly to 25 degrees C. The products were analyzed for composition and content of glycidol equivalents. The results are summarized below and in FIG. 2:

| Example 3 | Free glycerol (FG) (w/w %) | Free fatty acids FFA (w/w %) | Monoglyceride MAG (w/w %) | Diglyceride DAG (w/w %) | Triglyceride TAG (w/w %) | Glycidol eq. (ppm) |
|---|---|---|---|---|---|---|
| 0 h | 0.5 | 0.7 | 98.1 | 0.8 | 0.0 | 12.8 |
| 4 h | 0.6 | 0.7 | 97.2 | 1.5 | 0.0 | 3.6 |
| 8 h | 0.7 | 0.7 | 96.5 | 2.1 | 0.0 | 1.0 |
| 12 h | 0.9 | 0.9 | 95.2 | 3.1 | 0.0 | 0.5 |

Conclusion

Glycidol was reduced significantly after 8 hours, however the content of MAG was reduced from 98.1% to 95.2% which is a reduction of the quality of the finished product.

Example 4: Glycidol Reducing Effect of Different Solid Acidic Materials

Figure 3:
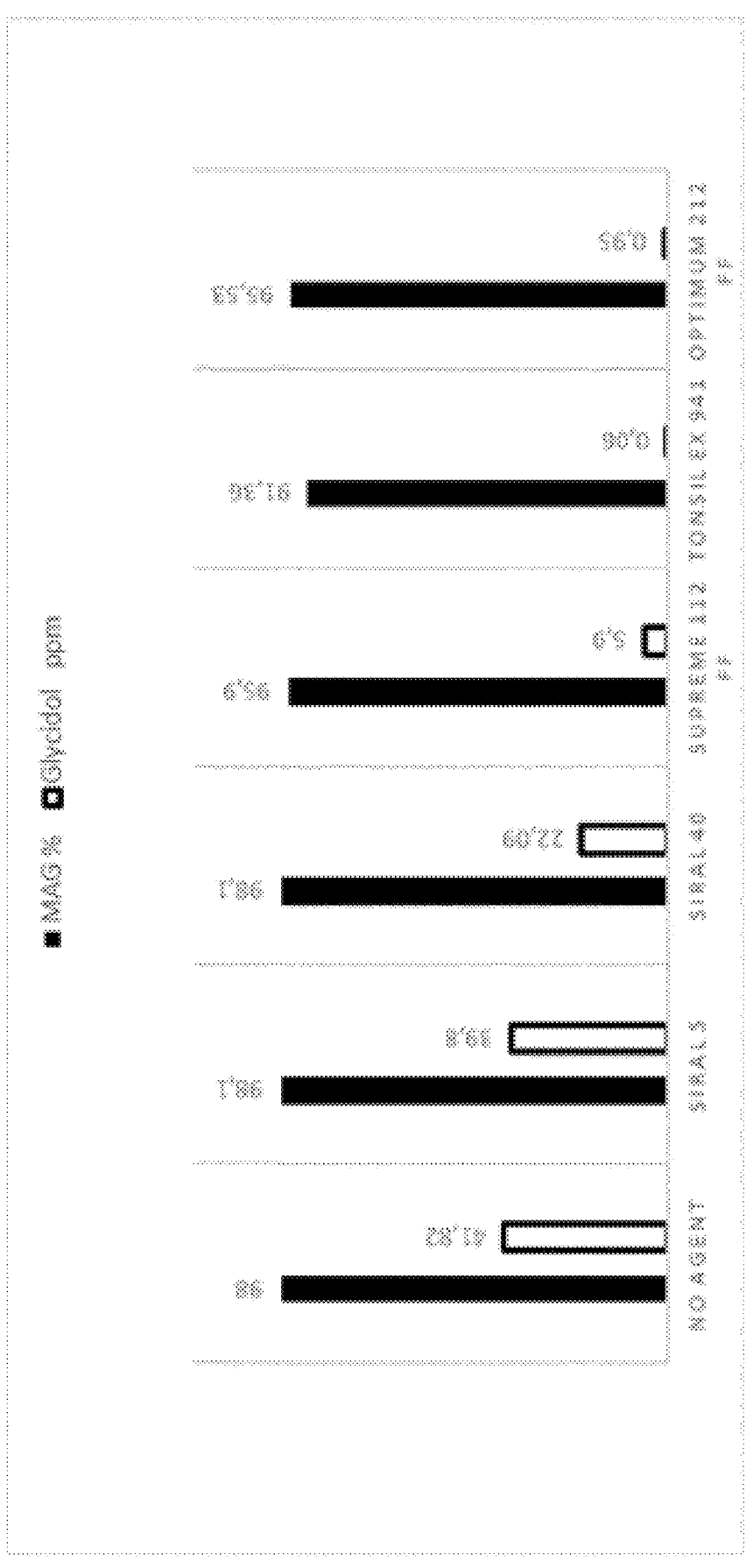
FIG. 3 shows different solid acidic materials affect the glycidol content and the content of MAG.

The product from example 1d) was heated to 110 degrees C. and 1% or 2% of heterogenous catalyst was added and the mixture was agitated at 110 degrees C. for 10 min under $N_2$. The catalyst was removed by filtration and the reaction mixture was cooled rapidly to 25 degrees C. The products were analyzed for composition and content of glycidol equivalents. The results are summarized below and illustrated in FIG. 3:

| Example 4 | Free glycerol (FG) (w/w %) | Free fatty acids FFA (w/w %) | Monoglyceride MAG (w/w %) | Diglyceride DAG (w/w %) | Triglyceride TAG (w/w %) | Glycidol eq. (ppm) |
|---|---|---|---|---|---|---|
| No agent | 0.3 | 0.9 | 98.0 | 0.9 | 0.0 | 41.82 |
| Siral 5 (1%) | 0.3 | 0.8 | 98.1 | 0.8 | 0.0 | 39.80 |
| Siral 40 (1%) | 0.3 | 0.9 | 98.1 | 0.8 | 0.0 | 22.09 |
| Supreme 112 FF (1%) | 0.6 | 0.9 | 95.9 | 2.6 | 0.0 | 5.90 |
| Tonsil EX941 (2%) | 1.93 | 0.31 | 91.36 | 6.4 | 0 | 0.06 |
| Optimum 212 FF (2%) | 1.28 | 0.28 | 95.53 | 2.91 | 0 | 0.95 |

Conclusion

The reduction of glycidol is accelerated by addition of various acid catalysts, however the MAG content is reduced at different rates depending on the type of acid catalyst applied.

Figure 4:
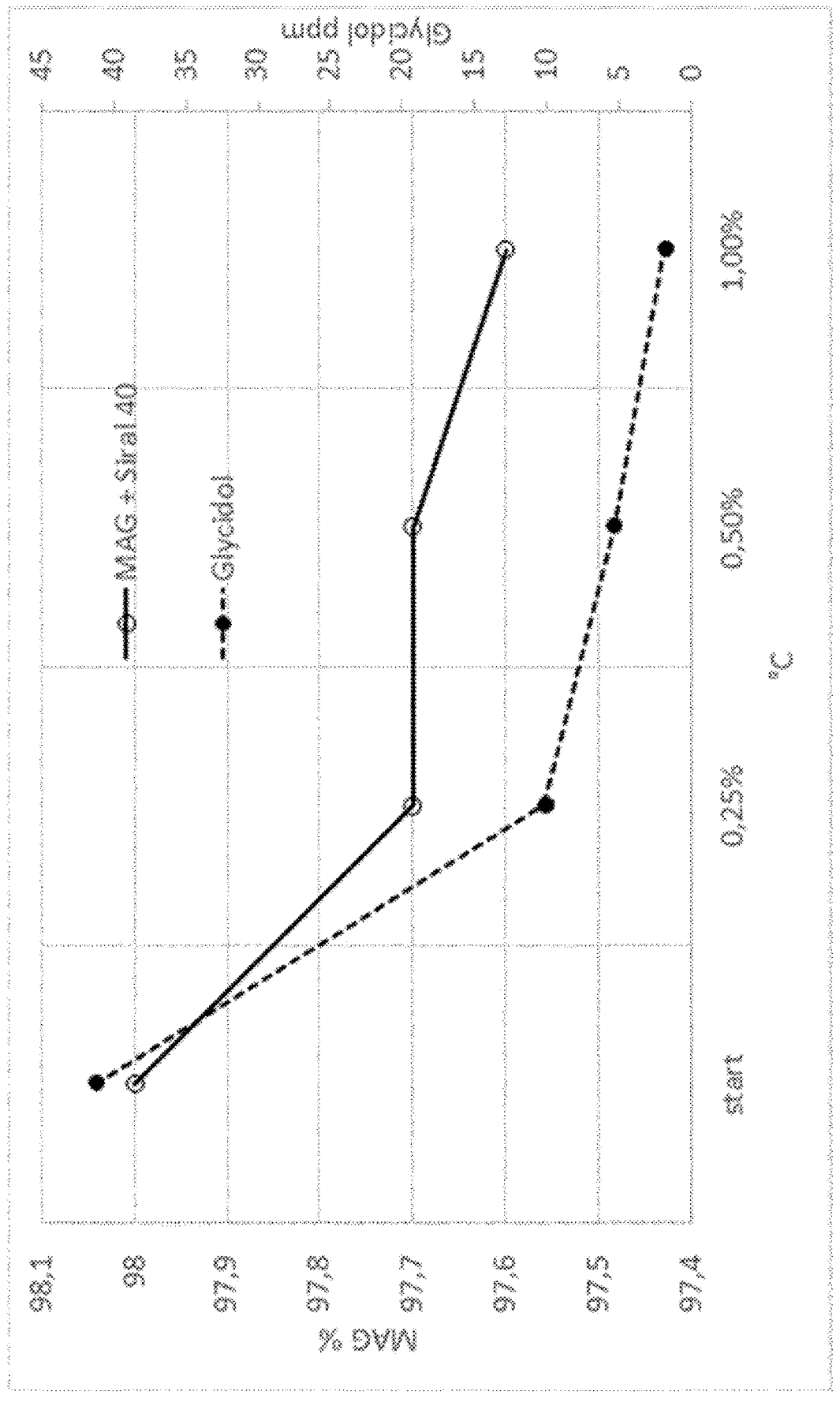
FIG. 4 shows how the dosage of the solid acidic material Siral 40 affects the glycidol content and the content of monoglyceride (MAG).
Figure 5:
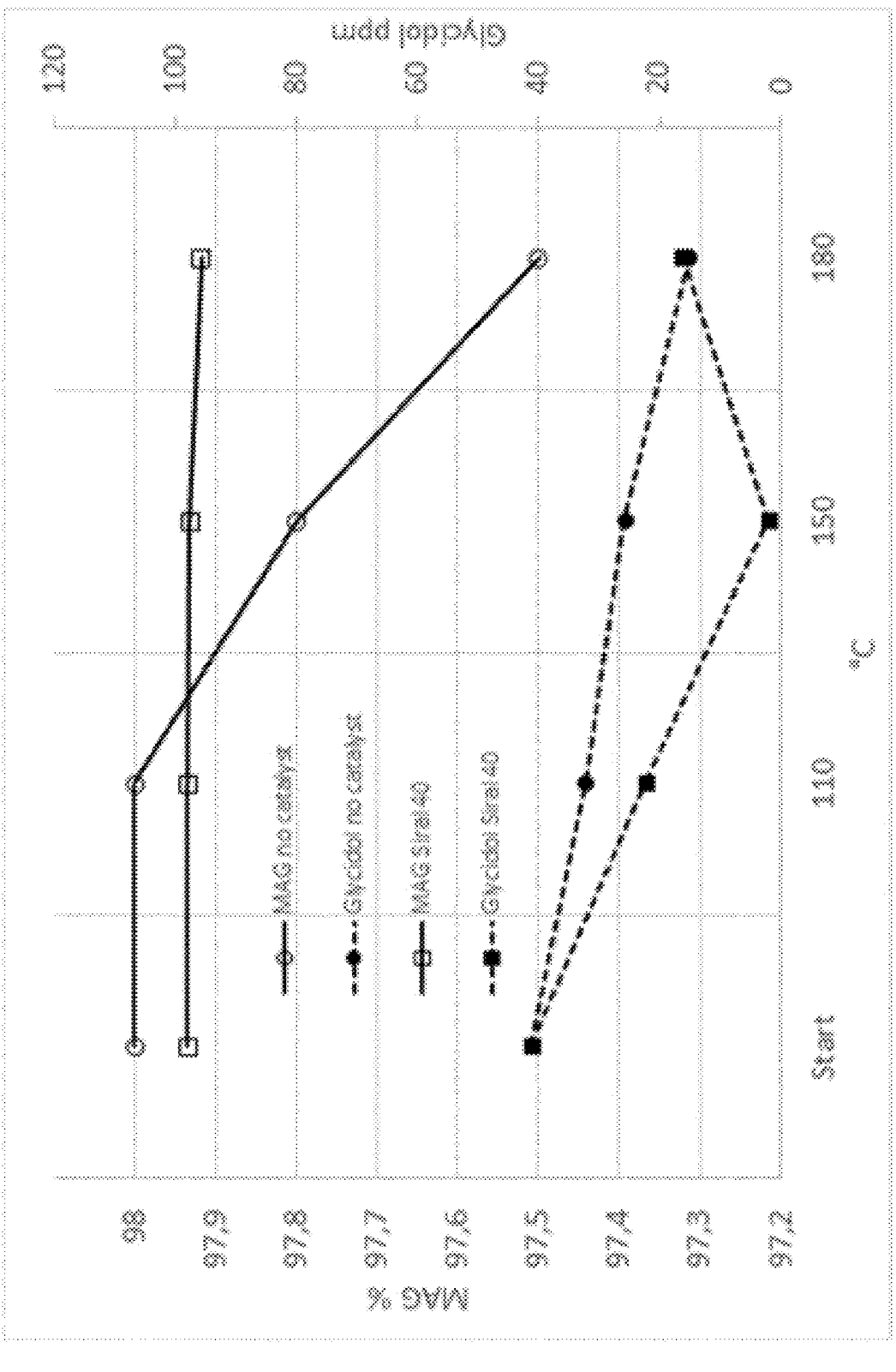
FIG. 5 shows the synergy between thermal treatment and solid acidic material (Siral 40) at different temperatures.

Example 5: Impact of the Concentration of Solid Acidic Material in Glycidol Removal The product from example 1d) was heated to 110 degrees C. and 0.25, 0.50 or 1.00% Siral 40 was added and the mixture was agitated at 110 degrees C. for 10 min under $N_2$. The catalyst was removed by filtration and the reaction mixture was cooled rapidly to 25 degrees C. The products were analyzed for composition and content of glycidol equivalents. The results are summarized below and illustrated in FIG. 4:

| Example 5 | Free glycerol (FG) (w/w %) | Free fatty acids FFA (w/w %) | Monoglyceride MAG (w/w %) | Diglyceride DAG (w/w %) | Triglyceride TAG (w/w %) | Glycidol eq. (ppm) |
|---|---|---|---|---|---|---|
| start | 0.3 | 0.9 | 98.0 | 0.9 | 0.0 | 41.30 |
| 0.25 | 0.3 | 0.9 | 97.7 | 1.1 | 0.0 | 10.20 |
| 0.5 | 0.3 | 0.9 | 97.7 | 1.1 | 0.0 | 5.39 |
| 1 | 0.3 | 0.9 | 97.6 | 1.2 | 0.0 | 1.85 |

Conclusion

The reduction of glycidol is significantly increased with higher amounts of Siral 40 but only very limited degradation of MAG is observed.

Example 6: Synergy Between Thermal Treatment and Solid Acidic Material in a Low Glycerol Environment The product from example 1d) was heated to 110, 150 or 180 degrees C. and 1.00% Siral 40 was added and the mixture was agitated at 110, 150 or 180 degrees C. for 10 min under $N_2$. The catalyst was removed by filtration and the reaction mixture was cooled rapidly to 25 degrees C. Reference trials for each temperature were performed using the exact same procedure without catalyst addition. The products were analyzed for composition, total Lovibond color and content of glycidol equivalents. The results are summarized below:

| Ex. 6 | Siral 40 | FG (w/w %) | FFA (w/w %) | MAG (w/w %) | DAG (w/w %) | TAG (w/w %) | Lovibond Red | Lovibond Yellow | Glycidol Eq. (ppm) |
|---|---|---|---|---|---|---|---|---|---|
| Start | | 0.3 | 0.9 | 98.0 | 0.9 | 0.0 | 0.2 | 0.7 | 41.30 |
| 110 | | 0.3 | 0.9 | 98.0 | 0.9 | 0.0 | 0.2 | 0.7 | 32.28 |
| 110 | X | 0.6 | 0.9 | 98.0 | 0.9 | 0.0 | 0.1 | 0.5 | 22.37 |
| 150 | | 0.3 | 0.9 | 97.8 | 1.0 | 0.0 | 0.7 | 1.7 | 25.86 |
| 150 | X | 0.3 | 0.9 | 97.6 | 1.2 | 0.0 | 0.1 | 0.6 | 2.10 |
| 180 | | 0.3 | 0.8 | 97.5 | 1.4 | 0.0 | 1 | 1.6 | 15.26 |
| 180 | X | 0.6 | 0.8 | 95.6 | 3.0 | 0.0 | 0.2 | 0.9 | 16.31 |

Conclusion

This example shows that the degradation of glycidol at 110 to 180 deg C. is accelerated and the degradation of MAG is reduced by addition of Siral 40. Furthermore the Lovibond red and yellow colors are reduced at 150 and 180 deg C. by addition of Siral 40.

Example 7: Thermal Treatment Before and After Distillation

1) A product was prepared as described in steps a) and b) of Example 1 and a sample of the step b)-product was taken under $N_2$ then cooled rapidly to 25 degrees C. The sample was analyzed for glycidol.
2) The product from step 1) was heated to 150 degrees C. under $N_2$ for a duration of 60 min. A sample was taken under $N_2$ then cooled rapidly to 25 degrees C. The sample was analyzed for glycidol.
3) The product of step 2) was distilled as described in steps c) and d) of Example 1. A sample of the resulting product was taken under $N_2$ then cooled rapidly to 25 degrees C. The sample was analyzed for glycidol.

4) The product from step 3) was heated to 100 degrees C. under $N_2$. Samples were taken at 240, 480, 720 and 1440 min under $N_2$ then cooled rapidly to 25 degrees C. The products were analyzed for composition and content of glycidol equivalents. The results are summarized below.

| Example 7 | Glycidol eq. (ppm) |
|---|---|
| 1) | 66.7 |
| 2) | 5.7 |
| 3) | 7.4 |
| 4) 240 min | 5.3 |
| 4) 480 min | 4.2 |
| 4) 720 min | 3.5 |
| 4) 1440 min | 2.0 |

Conclusion

The inventors have found that it is beneficial to apply the thermal treatment at multiple stages in the monoglyceride production process.

Example 8: Thermal Treatment Before Distillation Followed by Treatment by Solid Acidic Material 1) A product was prepared as described in steps a) and b) of Example 1 and a sample of the step b)-product was taken under $N_2$ then cooled rapidly to 25 degrees C. The sample was analyzed for glycidol.
2) The product from step 1) was heated to 150 degrees C. under $N_2$ for a duration of 60 min. A sample was taken under $N_2$ then cooled rapidly to 25 degrees C. The sample was analyzed for glycidol.
3) The product of step 2) was distilled as described in step c) and d) of Example 1. A sample of the step d) product was taken under $N_2$ then cooled rapidly to 25 degrees C. The sample was analyzed for glycidol.
4) The product from step 3) was heated to 150 degrees C. and 1 w/w % Siral 40 was added and the mixture was agitated at 150 degrees C. for 10 min under $N_2$. The Siral 40 was subsequently removed by filtration and the reaction mixture was cooled rapidly to 25 degrees C. The products were analyzed for their content of glycidol equivalents.

| Example XY | Glycidol eq. (ppm) |
|---|---|
| a) | 68.0 |
| b) | 6.9 |
| c) | 9.1 |
| d) | 1.2 |

Conclusion

The inventors have found that it is beneficial to apply the thermal treatment before distillation followed by treatment with SIRAL 40 after distillation.

Example 9. Large Scale Production—Thermal Treatment Before Distillation

Figure 6:
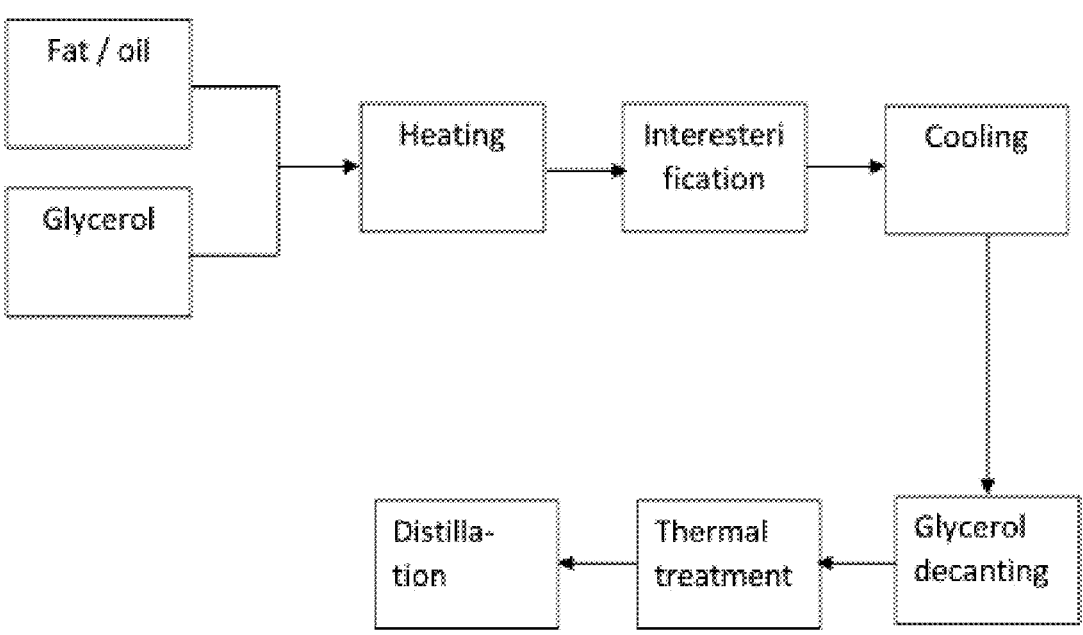
FIG. 6 depicts an outline of a thermal treatment before distillation process setup for an industrial monoglyceride/mono-diglyceride production plant to demonstrate an embodiment of the invention in large scale.

A series of experiments were conducted in an industrial monoglyceride/mono-diglyceride production plant to demonstrate the method of the invention in large scale. An outline of the process setup is shown in FIG. 6.

The thermal treatment unit was inserted after the glycerol decanting since this is expected to provide the best product quality of the finished product. The thermal treatment was performed as a continuous process using an intermediate tank that could hold an amount corresponding to 2 hours flow of intermediate product to the distillation plant. The tank was a standard non-agitated stainless steel type with protective nitrogen atmosphere. The intermediate product from decanting was heated through a plate heat exchanger and fed into the top of the tank onto the inner sidewall of the tank to minimize mixing with the product in the tank. The product was pumped out from the bottom of the tank and into the normal distillation process. The thermal treatment time was regulated by controlling the amount in the tank with the inlet and outlet pumps. The amount in the tank was measured by a standard radar level sensor. Alternatively a weighing cell could be used. The optimal thermal treatment conditions in the plant was approx 110-130 minutes at approx. 150-160 degrees C.

The following typical results were obtained based on average values from 3 separate experiments with each monoglyceride-containing composition.

| Oil source | Glycidol eq. (ppm) Before thermal treatment (see FIG. 6) | Glycidol eq. (ppm) After thermal treatment (see FIG. 6) | Glycidol eq. (ppm) After distillation of monoglyceride (see FIG. 6) |
|---|---|---|---|
| High Oleic Sunflower oil | 87.3 | 2.1 | 2.9 |
| Sunflower oil | 51.2 | 3.1 | 3.9 |
| Palm oil | 67.9 | 2.9 | 3.2 |
| Palm kernel oil | 58.1 | 2.7 | 2.0 |
| Rape Seed Oil | 4.2 | 2.1 | 1.0 |
| Fully hydrogenated palm oil IV < 2 | 57.1 | 5.9 | 6.2 |

Conclusion: The inventors have demonstrated that the thermal treatment process can be applied to monoglyceride compositions based on various raw materials and that it can be implemented in large scale.

Example 10. Large Scale Production—Thermal Treatment after Distillation

Figure 7:
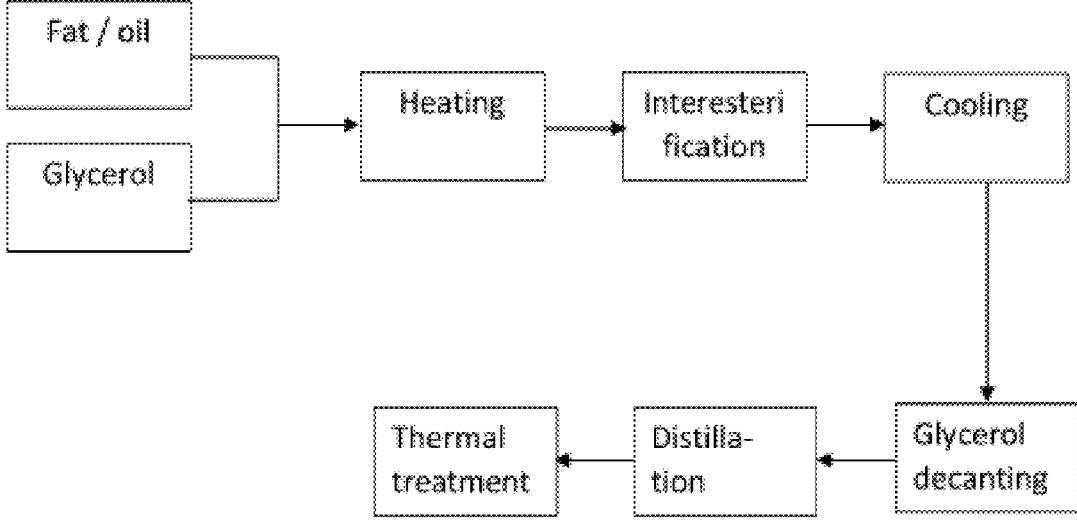
FIG. 7 depicts an outline of a thermal treatment after distillation process setup for an industrial monoglyceride/mono-diglyceride production plant to demonstrate an embodiment of the invention in large scale.

A series of experiments were conducted in an industrial monoglyceride/mono-diglyceride production plant to demonstrate the method of the invention in large scale. An outline of the process setup is shown in FIG. 7.

The thermal treatment unit was inserted after the distillation unit to demonstrate the possibility for removing glycidol from a distilled monoglyceride product. The thermal treatment was operated as a continuous process using an intermediate tank that can hold an amount corresponding to 2 hours flow of intermediate product to the distillation plant. The tank was a standard non-agitated stainless steel type with protective nitrogen atmosphere. The distilled product was heated through a plate heat exchanger and fed into the top of the tank onto the inner sidewall of the tank to minimize mixing with the product in the tank. The product was pumped out from the bottom of the tank prior to analysis. The thermal treatment time was regulated by controlling the amount in the tank with the inlet and outlet pumps. In the examples below, the thermal treatment involved a reaction time of 2 hours and a thermal treatment temperature of 155 degrees C.

The following typical results were obtained based on average values from 2 separate experiments with each monoglyceride-containing composition.

| Oil source | Glycidol eq. (ppm) After distillation of monoglyceride (see FIG. 7) | Glycidol eq. (ppm) After thermal treatment (see FIG. 7) |
|---|---|---|
| High Oleic Sunflower oil | 72.3 | 4.7 |
| Palm oil | 55.3 | 7.2 |
| Rape Seed Oil | 5.3 | 2.6 |
| Fully hydrogenated palm oil IV < 2 | 66.8 | 8.9 |

Conclusion: The inventors have demonstrated that the thermal treatment process can be applied to distilled monoglyceride compositions based on various raw materials and that it can be implemented in large scale32.

The invention claimed is:

1. A method of producing a monoglyceride-containing product comprising at least 90% w/w monoglyceride and having a content of glycidol equivalents of at most 10 ppm, the method comprising
   step i) of thermally treating a first monoglyceride-containing composition (mcc1) comprising at least 25% w/w monoglyceride and a total content of glycidol equivalents of at least 15 ppm, said thermal treatment involves heating the monoglyceride-containing composition to a temperature in the range of 90-210 degrees C. for a duration sufficient to reduce the total content of glycidol equivalents by at least 50%, and/or
   step ii) of contacting a second monoglyceride-containing composition (mcc2) comprising at least 25% w/w monoglyceride and a total content of glycidol equivalents of at least 15 ppm with a solid acidic material.

2. The method according to claim 1, wherein the thermal treatment of step i) involves heating the first monoglyceride-containing composition to a temperature in the range of 120-170 degrees C.

3. The method according to claim 1, wherein the thermal treatment of step i) involves heating the first monoglyceride-containing composition for a duration sufficient to reduce the total content of glycidol equivalents of the mcc by at least 70%.

4. The method according to claim 1, wherein the thermal treatment of step i) and/or step ii) is performed using an inert atmosphere.

5. The method according to claim 1, wherein the solid acidic material of step ii) is used in an amount of 0.1-10 w/w % relative to the weight of the monoglyceride-containing composition.

6. The method according to claim 1, wherein the solid acidic material of step ii) provides a pH of at most 5 when 10 g of the solid acidic material is mixed in 100 ml demineralised water at 25 degrees C. and allowed to equilibrate for 10 minutes.

7. The method according to claim 1, wherein step ii) involves heating the second monoglyceride-containing composition to a temperature in the range of 50-180 degrees C.

8. The method according to claim 1, wherein the solid acidic material of step ii) is selected from one or more of the group consisting of zeolites, zeotypes, acid clays, metal oxides, mixed metal oxides, sulphated oxides, supported acids and cation exchange resins, and a combination thereof.

9. The method according to claim 1, wherein the first and/or second monoglyceride-containing composition comprises:
   at least 25% w/w monoglyceride,
   at least 15 ppm glycidol equivalents, and
   glycerol, diglyceride, and triglyceride.

10. The method according to claim 1, wherein the first and/or second mcc comprises one or more of:
   at least 30% w/w monoglyceride,
   at most 30% w/w glycerol,
   at most 30% w/w triglyceride,
   a total amount of monoglyceride and diglyceride of at least 50% w/w.

11. The method according to claim 1, wherein the first and/or second mcc comprises an amount of glycidol equivalents of at least 20 ppm.

12. The method according to claim 1, comprising one or more of:
   step i), or
   step ii), or
   both step i) and ii).

13. The method according to claim 1, wherein the monoglyceride-containing product is packaged in a suitable container.

14. The method according to claim 1, furthermore comprising the steps of:
   a) contacting glycerol with diglyceride and/or triglyceride at conditions sufficient to provide a reacted mixture comprising:
      at least 25% w/w monoglyceride,
      at least 1% w/w glycerol,
      diglyceride and/or triglyceride, and
      a content of glycidol equivalents of at least 1 ppm,
   b) subjecting a composition derived from the reacted mixture of step a) to a distillation to remove an amount of glycerol, thereby providing a first distillate enriched with respect to glycerol, and a first distillation residue enriched with respect to monoglyceride, c) optionally, subjecting the first distillation residue to a distillation to further enrich monoglyceride thereby providing a second distillate enriched with respect to monoglyceride and a second distillation residue depleted with respect to diglyceride,
   d) optionally, further purifying the first distillation residue and/or the second distillate,
   and recovering the first distillation residue of step b), the second distillate of step c), or a further purified composition of step d) as the monoglyceride-containing product, and wherein the first and/or second monoglyceride-containing composition is a composition derived from step a), b), c), or d).

15. The method according to claim 14, wherein the reacted mixture of step a) comprises:
   25-60% w/w monoglyceride,
   10-50% w/w diglyceride,
   1-30% w/w triglyceride,
   1-25% w/w glycerol,
   0-10% w/w free fatty acids, and
   a content of glycidol equivalents of at least 15 ppm.

16. The method according to claim 14, wherein the reacted mixture of step a) comprises an amount of glycidol equivalents of at least 20 ppm.

17. The method according to claim 14, wherein the reacted mixture of step a) has a total amount of monoglyceride and diglyceride of at least 50% w/w.

18. The method according to claim 14, wherein the composition derived from the reacted mixture of step a) provided in step b) comprises:
   25-80% w/w monoglyceride,
   10-50% w/w diglyceride,
   1-30% w/w triglyceride,
   1-25% w/w glycerol,
   0-10% w/w free fatty acids, and
   a content of glycidol equivalents of at least 15 ppm.

19. The method according to claim 14, comprising at least step i) and wherein step i) performed is performed during or prior to step b).

20. The method according to claim 14, comprising at least step i) and step c) and wherein step i) performed is performed prior to the distillation of step c).

21. The method according to claim 14, comprising at least step ii) and wherein step ii) performed is after step b).

22. The method according to claim 1, wherein the monoglyceride-containing product has a content of glycidol equivalents of at most 5 ppm.

23. The method according to claim 1, wherein the monoglyceride-containing product has an iodine value of at least 20.

24. The method according to claim 1, wherein the monoglyceride-containing product has a peroxide value of at most 10 meq/kg.

25. A monoglyceride-containing product, comprising:
   at least 90% w/w monoglyceride,
   a content of glycidol equivalents of at most 10 ppm,
and having:
   a peroxide value of at most 10 meg/kg.

26. A monoglyceride-containing product according to claim 25 comprising:

at least 95% w/w monoglyceride, a content of glycidol equivalents of at most 5 ppm, and having:

a peroxide value of at most 5 meq/kg.

27. The monoglyceride-containing product according to claim 26, furthermore having an iodine value of at least 20.

\* \* \* \* \*